:::: {align=center}
(12) United States Patent
Fischer et al.

(10) Patent No.: US 8,585,710 B2
(45) Date of Patent: Nov. 19, 2013
::::

(54) SURGICAL INSTRUMENT FOR DETERMINING THE SIZE OF INTERVERTEBRAL IMPLANT

(75) Inventors: Kay Fischer, Tuttingen (DE); Susanne Schneid, Neu-Ulm (DE); Robert Schultz, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 1434 days.

(21) Appl. No.: 11/715,557

(22) Filed: Mar. 8, 2007

(65) Prior Publication Data

US 2007/0209222 A1    Sep. 13, 2007

Related U.S. Application Data

(63) Continuation of application No. PCT/EP2005/009021, filed on Aug. 20, 2005.

(30) Foreign Application Priority Data

Sep. 8, 2004    (DE) .......................... 10 2004 043 995

(51) Int. Cl.
    *A61B 17/56*    (2006.01)
(52) U.S. Cl.
    USPC ............................................. 606/102; 606/90
(58) Field of Classification Search
    USPC ............ 33/511–512; 600/201, 219–220, 239;
                606/61, 90, 99, 102, 105; 623/17.11,
                                              623/17.16
    See application file for complete search history.

(56) References Cited

U.S. PATENT DOCUMENTS

| 4,997,432 | A |   | 3/1991  | Keller |            |
|-----------|---|---|---------|--------|------------|
| 5,122,130 | A | * | 6/1992  | Keller | ........................ 606/86 A |
| 5,716,360 | A | * | 2/1998  | Baldwin et al. | ................. 606/80 |
| 6,143,033 | A |   | 11/2000 | Paul et al. |   |
| 6,179,873 | B1 |  | 1/2001  | Zientek |   |

(Continued)

FOREIGN PATENT DOCUMENTS

| DE | 201 16 410 U1 | 11/2001 |
| EP | 0 333 990 B1  | 9/1989  |

(Continued)

OTHER PUBLICATIONS

International Search Report of PCT/EP2005/009021, dated Nov. 29, 2005 (with translation).

(Continued)

*Primary Examiner* — Nicholas Woodall
*Assistant Examiner* — Larry E. Waggle, Jr.
(74) *Attorney, Agent, or Firm* — RatnerPrestia

(57)    ABSTRACT

A surgical instrument is configured for determining the size and/or height of an intervertebral implant insertable into an intervertebral space between two adjacent vertebral bodies of two human or animal vertebrae. The implant includes a first abutment element for abutment against an articular surface of one of the two adjacent vertebral bodies and a second abutment element supported directly or indirectly on the first abutment element for abutment against an articular surface of the other of the two adjacent vertebral bodies. The instrument includes a holding part defining a longitudinal direction and at least one test implant, which includes a first and a second test-implant abutment element each having at least one abutment surface for abutment against one of the articular surfaces. A distal end of the holding part includes at least one abutment-element holding element for detachable connection to the at least one test implant 149.

25 Claims, 4 Drawing Sheets

(56) References Cited

U.S. PATENT DOCUMENTS

| | | | |
|---|---|---|---|
| 6,652,533 B2 * | 11/2003 | O'Neil | 606/100 |
| 6,712,825 B2 * | 3/2004 | Aebi et al. | 606/90 |
| 6,740,119 B2 | 5/2004 | Ralph et al. | |
| 6,755,841 B2 * | 6/2004 | Fraser et al. | 606/99 |
| 7,118,580 B1 * | 10/2006 | Beyersdorff et al. | 606/99 |
| 7,169,153 B2 * | 1/2007 | Keller | 606/99 |
| 7,419,505 B2 * | 9/2008 | Fleischmann et al. | 623/17.11 |
| 7,547,309 B2 * | 6/2009 | Bertagnoli et al. | 606/99 |
| 7,588,573 B2 * | 9/2009 | Berry | 606/86 A |
| 7,594,919 B2 * | 9/2009 | Peterman | 606/99 |
| 2002/0072752 A1 * | 6/2002 | Zucherman et al. | 606/99 |
| 2003/0069586 A1 * | 4/2003 | Errico et al. | 606/99 |
| 2003/0078590 A1 * | 4/2003 | Errico et al. | 606/102 |
| 2003/0135217 A1 * | 7/2003 | Buttermann et al. | 606/79 |
| 2004/0098129 A1 | 5/2004 | Lin | |
| 2004/0148027 A1 | 7/2004 | Errico et al. | |
| 2004/0167625 A1 | 8/2004 | Beyar et al. | |
| 2004/0220582 A1 | 11/2004 | Keller | |
| 2005/0149047 A1 * | 7/2005 | Parry et al. | 606/99 |

FOREIGN PATENT DOCUMENTS

| | | |
|---|---|---|
| EP | 1 222 903 A1 | 7/2002 |
| GM | 8016889 | 9/1980 |
| JP | 2004-516907 | 6/2004 |
| WO | WO 97/06753 | 2/1997 |
| WO | WO 00/44321 | 8/2000 |
| WO | WO 03/092507 A2 | 11/2003 |
| WO | WO 2004/039291 A | 5/2004 |

OTHER PUBLICATIONS

English Translation of PCT Written Opinion of the International Searching Authority for PCT/EP/2005/009021 Dated Mar. 22, 2007.
Office Action for Japanese Patent Application No. JP 2007-530609, prepared Sep. 30, 2010 (with English language translation).

* cited by examiner

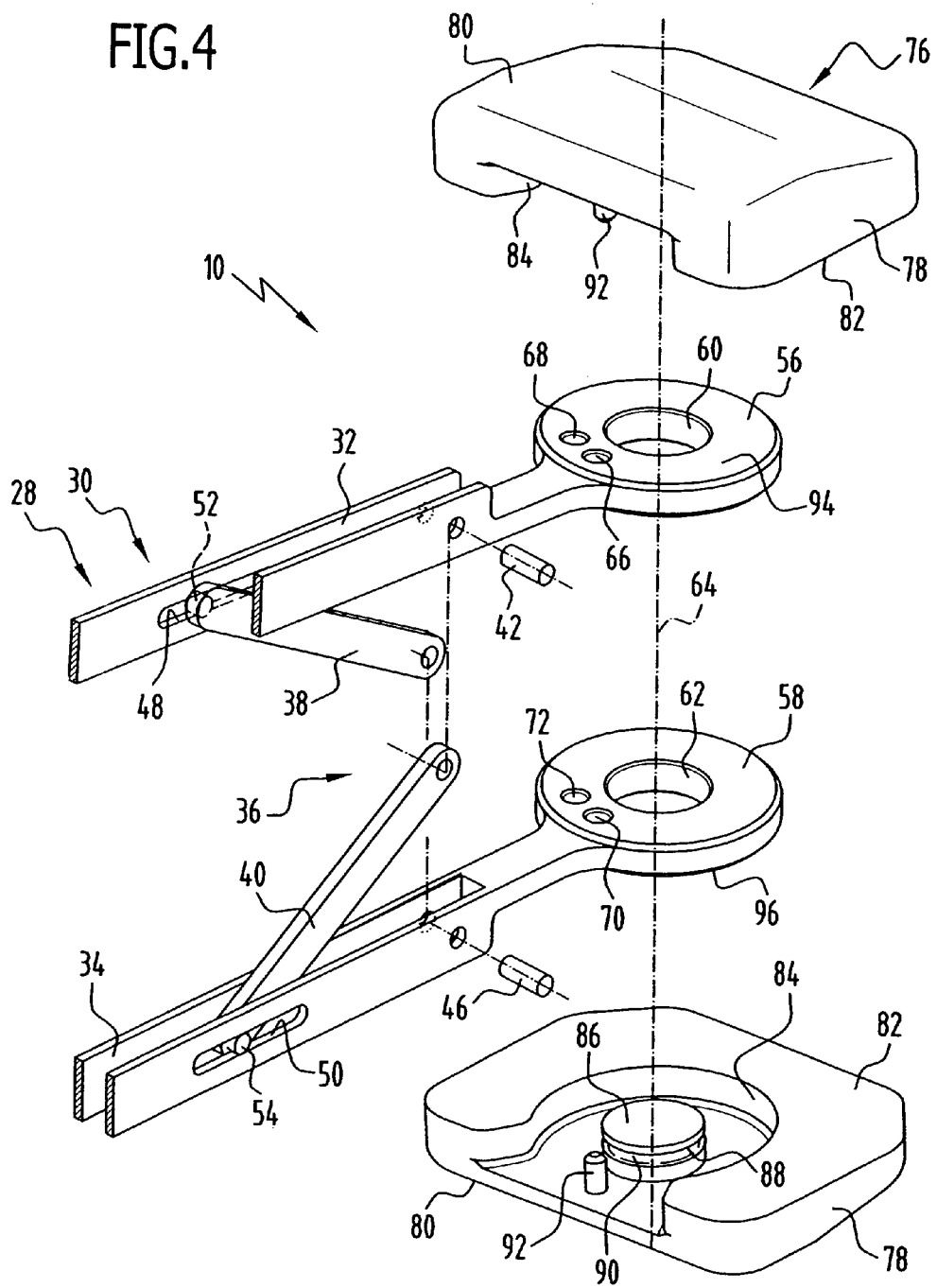

SURGICAL INSTRUMENT FOR DETERMINING THE SIZE OF INTERVERTEBRAL IMPLANT

Pursuant to 35 U.S.C. §365(c), this application is a continuation application of International Patent Application number PCT/EP2005/009021 filed on Aug. 20, 2005 and designating the United States, which claims priority to the contents of German application number 10 2004 043 995.8 filed Sep. 8, 2004, which are incorporated herein by reference in their entirety and for all purposes.

BACKGROUND OF THE INVENTION

The present invention relates to a surgical instrument for determining the size and/or height of an intervertebral implant insertable into an intervertebral space between two adjacent vertebral bodies of two vertebrae of a human or animal spinal column, wherein the intervertebral implant comprises a first abutment element for abutment against an articular surface of one of the two adjacent vertebral bodies as well as a second abutment element supported directly or indirectly on the first abutment element for abutment against an articular surface of the other of the two adjacent vertebral bodies, wherein the instrument comprises a holding part defining a longitudinal direction and at least one test implant, which comprises a first and a second test-implant abutment element each having at least one abutment surface for abutment against one of the articular surfaces, wherein provided on a distal end of the holding part is at least one abutment-element holding element for detachable connection to the at least one test implant.

The treatment of degenerative diseases in the region of the spinal column very often involves the surgical removal of intervertebral disk tissue. Adjacent motion segments, i.e. adjacent vertebral bodies, are then fused by means of a bone chip and/or artificial intervertebral implants. An alternative to the fusion of adjacent vertebral bodies is to implant artificial intervertebral disks, by means of which a mobility of adjacent vertebral bodies relative to one another may be at least partially maintained.

An artificial intervertebral disk is used, inter alia, to restore the original intervertebral disk height and re-stabilize the spinal column.

For determining the required size and/or height of the intervertebral implant, various instruments or test implants are known, which are introduced into the cleared intervertebral space to determine the size and height. In dependence upon the size and height of the implant determined by means of the instrument and/or test implant, the actual intervertebral implant is selected and then implanted.

Therefore, it is desirable to improve an instrument of the initially described type in a way that allows the size and/or height of an intervertebral implant to be determined in a simple and different manner.

SUMMARY OF THE INVENTION

It is proposed in a surgical instrument of the initially described type, that the first and/or the second test-implant abutment element in relation to the longitudinal direction is detachably connectable to the at least one abutment-element holding element in at least two defined, different angular positions relative thereto.

The development according to the invention makes it possible to connect the test-implant abutment element to the abutment-element holding element in at least two different angular positions. This allows the test implant to be introduced at different angles into the intervertebral space. In other words, it is possible to introduce the test implant not only through e.g. an anterior approach but also through a lateral approach. An approach to the intervertebral space is therefore freely selectable and for this purpose the test-implant abutment elements are connected by the holding part either in a first or in another angular position to the abutment-element holding element. There is therefore no longer any need for compromises with regard to the natural or optimum angular position during introduction of the test implant. A patient may be positioned in an optimum manner. The instrument according to the invention may then be suitably adjusted in accordance with the operating conditions. What is more, the detachable connection of the test-implant abutment elements to the at least one abutment-element holding element allows different test implants of differing heights and/or lordosis angles, i.e. angles between the abutment surfaces, to be connected to the holding part. Thus, only one holding part with corresponding test-implant abutment elements is needed to model a plurality of test implants and introduce these through different approaches into the intervertebral space.

It is advantageous when the first or the second test-implant abutment element in the at least two defined, different angular positions is disposed lying in each case in a common plane and that the two planes are identical. In other words, this means that the first or the second test-implant abutment element is transferable quasi by means of a purely geometric rotation from the first angular position to the second angular position. However, the instrument need not be designed in such a way that the transfer from the first angular position to the second angular position is possible directly through a rotation. A translational-rotational-translational movement may also be necessary.

It is advantageous when the first and/or the second test-implant abutment element and the at least one abutment-element holding element, for detachable connection to one another, can be brought into engagement by means of a relative movement towards one another in a connection direction extending transversely of the longitudinal direction. When the test implant is introduced into the intervertebral space, this development prevents shear and tensile forces, which act typically in longitudinal direction, from possibly leading to detachment of the test implant from the holding part.

Advantageously, the at least one abutment-element holding element is non-positively and/or positively connectable to the first and/or to the second test-implant abutment element. In this way, a secure connection may easily be formed between the abutment-element holding element and the at least one test-implant abutment element.

The construction of the instrument becomes particularly simple when a first and a second connection element are provided for connecting the at least one abutment-element holding element to the first and/or to the second test-implant abutment element and when one of the test-implant abutment elements and the at least one abutment-element holding element each carry one of the two connection elements. For example, by bringing the two connection elements together or into engagement, a secure connection may be established between the at least one abutment-element holding element and the first and/or the second test-implant abutment element.

The construction of the instrument becomes particularly simple when the first connection element is a receiver and the second connection element is a projection, which corresponds to the receiver and is can be introduced therein.

It is advantageous when the projection is a cylindrical pin, which projects from the test-implant abutment element in the direction of the abutment-element holding element, and when the receiver is a bore or blind hole bore corresponding in diameter to the pin. This simplifies the design and manufacture of the instrument as well as exchange of the test-implant abutment elements.

In order to prevent unintentional detachment of the test-implant abutment elements from the at least one abutment-element holding element as a result of shear- and tensile forces in longitudinal direction of the holding part, it is advantageous when the projection can be introduced into the receiver in a direction transversely of the longitudinal direction.

A detent connection is advantageously provided for securing a connection of the at least one abutment-element holding element to the first and/or the second test-implant abutment element in one of the angular positions. By virtue of the detent connection, an unintentional detachment of the test-implant abutment element connected to the at least one abutment-element holding element can be prevented in a connection position.

In a preferred form of construction of the invention, a clamping device may be provided for clamping and securing a connection of the at least one abutment-element holding element to the first and/or the second test-implant abutment element in one of the angular positions. By virtue of the clamping device, an unintentional detachment of the test-implant abutment element from the at least one abutment-element holding element may be prevented.

It is advantageous when the clamping device comprises a clamping element, which at least partially embraces at least one of the connection elements and which is insertable into a gap between the at least one abutment-element holding element and the first and/or the second test-implant abutment element and before the connection of the at least one abutment-element holding element and the first and/or the second test-implant abutment element projects at least at one side beyond the gap. Preferably, a deformable, in particular an elastic clamping element may be used, so that clamping forces of the clamping element in the connection position act in the opposite direction upon the abutment-element holding element and the test-implant abutment element.

A particularly simple construction of the instrument arises when the gap comprises an annular groove running in peripheral direction around the projection and when the clamping element is an elastic ring, the diameter of which is larger than a depth of the annular groove. If, for example, a connection pin is provided with the annular groove, then directly during introduction of the pin into a corresponding receiver it is possible to achieve not only a connection but directly also a clamping between the two parts.

Advantageously, a clamping device is provided for clamping and securing a connection of the at least one abutment-element holding element to the first and/or the second test-implant abutment element in one of the angular positions.

It is advantageous when a plurality of test implants are provided and when the plurality of test implants have different distances between the abutment surfaces and/or different lordosis angles between the abutment surfaces. By virtue of the plurality of test implants it is possible by means of a single holding part to determine different implant sizes and implant heights as well as a lordosis angle required in each case between the abutment surfaces. As soon as the quantities to be determined are known, the intervertebral implant that is to be permanently implanted may be selected and inserted into the intervertebral space.

According to a preferred form of construction of the invention, it may be provided that an angle setting device is provided for defining and setting the different angular positions of the first and/or the second test-implant abutment element relative to the at least one abutment-element holding element, that the angle setting device comprises at least two setting elements that can be brought into engagement with one another in the different angular settings, and that the first and/or the second test-implant abutment element has a first setting element and the at least one abutment-element holding element has a second setting element. By means of the suitably arranged setting elements, defined angular settings of the test-implant abutment element and of the abutment-element holding element are preselectable in a desired manner.

It is particularly advantageous when at least one of the at least two setting elements is designed in the form of a setting receiver and when at least one other of the at least two setting elements is designed in the form of a setting projection which can be introduced into the setting receiver. An angular setting may then be preset in a simple manner by introducing the setting projection into the setting receiver. This results in a defined angular position of the abutment-element holding element relative to the test-implant abutment element.

In order to secure a desired angular position of the test-implant abutment element relative to the at least one abutment-element holding element, it is advantageous when the setting projection can be introduced into the setting receiver in a direction transversely of the longitudinal direction. If the holding part is moved in longitudinal direction, then shear- and tensile forces exerted thereby cannot result in the setting projection being movable relative to the setting receiver, in particular unintentionally disengaging therefrom.

The construction of the instrument is further simplified when the test-implant abutment element carries at least one setting projection and when the abutment-element holding element has at least two setting receivers. This makes it possible to introduce the at least one setting projection of the test-implant abutment element into one or the other of the at least two setting receivers and hence preset different angular positions of the test-implant abutment element relative to the at least one abutment-element holding element.

It is advantageous when the at least one abutment-element holding element is cylindrical in shape and when a longitudinal axis of the at least one abutment-element holding element extends transversely of the longitudinal direction. The abutment-element holding element is then particularly simple to manufacture and is easily connectable to a plurality of test-implant abutment elements.

It may further be advantageous when the test-implant abutment elements each have a recess for the at least one abutment-element holding element and when the at least one abutment-element holding element can be introduced positively or substantially positively into the recess. In this way, an additional hold and/or support of the test-implant abutment element relative to the abutment-element holding element may be achieved.

In order to introduce the test-implant into the intervertebral space through different, desired approaches in the human body, it is advantageous when the first and/or the second test-implant abutment element can be disposed in the second angular position relative to the at least one abutment-element holding element by being rotated through a setting angle relative to the first angular position. The setting angle may in each case be so selected that the test implant held on the holding part may be introduced in a desired manner, for example through a lateral or anterior approach.

The setting angle advantageously has a value in a range of 10° to 30°.

According to a preferred form of construction of the invention, it may be provided that a first and a second abutment-element holding element may be provided on the distal end of the instrument and that the first abutment-element holding element is detachably connectable to the first test-implant abutment element and the second abutment-element holding element is detachably connectable to the second test-implant abutment element. This allows the two abutment-element holding elements to be designed individually for connection to the test-implant abutment elements. In particular, they may differ in shape. It is moreover possible to form the abutment-element holding elements on the holding part such that they are inclined relative to one another, so that a lordosis angle is already definable by the abutment-element holding elements themselves.

So that the instrument may simultaneously be used also to distract adjacent vertebral bodies, it is advantageous when the first abutment-element holding element and the second abutment-element holding element are supported such that they are movable towards and/or away from one another transversely or substantially transversely of the abutment surfaces. It is thereby possible, on the one hand, to determine the size of the intervertebral implant to be inserted and the lordosis angle and, on the other hand, to vary a spacing between the abutment surfaces.

It may be advantageous when the distal end of the holding part has two spreading jaws, when the spreading jaws comprise or carry the abutment-element holding elements and when the spreading jaws are movable away from and/or towards one another by means of a drive device, which is disposed on the holding part and comprises an actuating element disposed on the proximal end of the holding part. According to this development, the holding part may be designed in the form of a spreading instrument, which has spreading jaws designed for connection to the test-implant abutment elements.

The spreading jaws are preferably supported such that they can be spread parallel to one another.

In order, given a variation of the spacing between the two test-implant abutment elements, also to be able to determine this spacing, it is advantageous when the holding part has a path measuring device for measuring and indicating a spacing between the abutment surfaces or a displacement of the abutment-element holding elements relative to one another. If, for example, the spacing between the abutment surfaces is known, then by means of the path measuring device a variation of the spacing may be determined and added to the known spacing. In this way, the number of required test-implant abutment elements can be reduced, as different heights may be set and determined by spreading the abutment-element holding elements.

BRIEF DESCRIPTION OF THE DRAWINGS

A more detailed explanation is provided by the following description of a preferred embodiment of the invention in connection with the drawings. The drawings show:

FIG. 4: an exploded view of the distal end of the instrument.

DETAILED DESCRIPTION OF THE INVENTION

Figure 1:
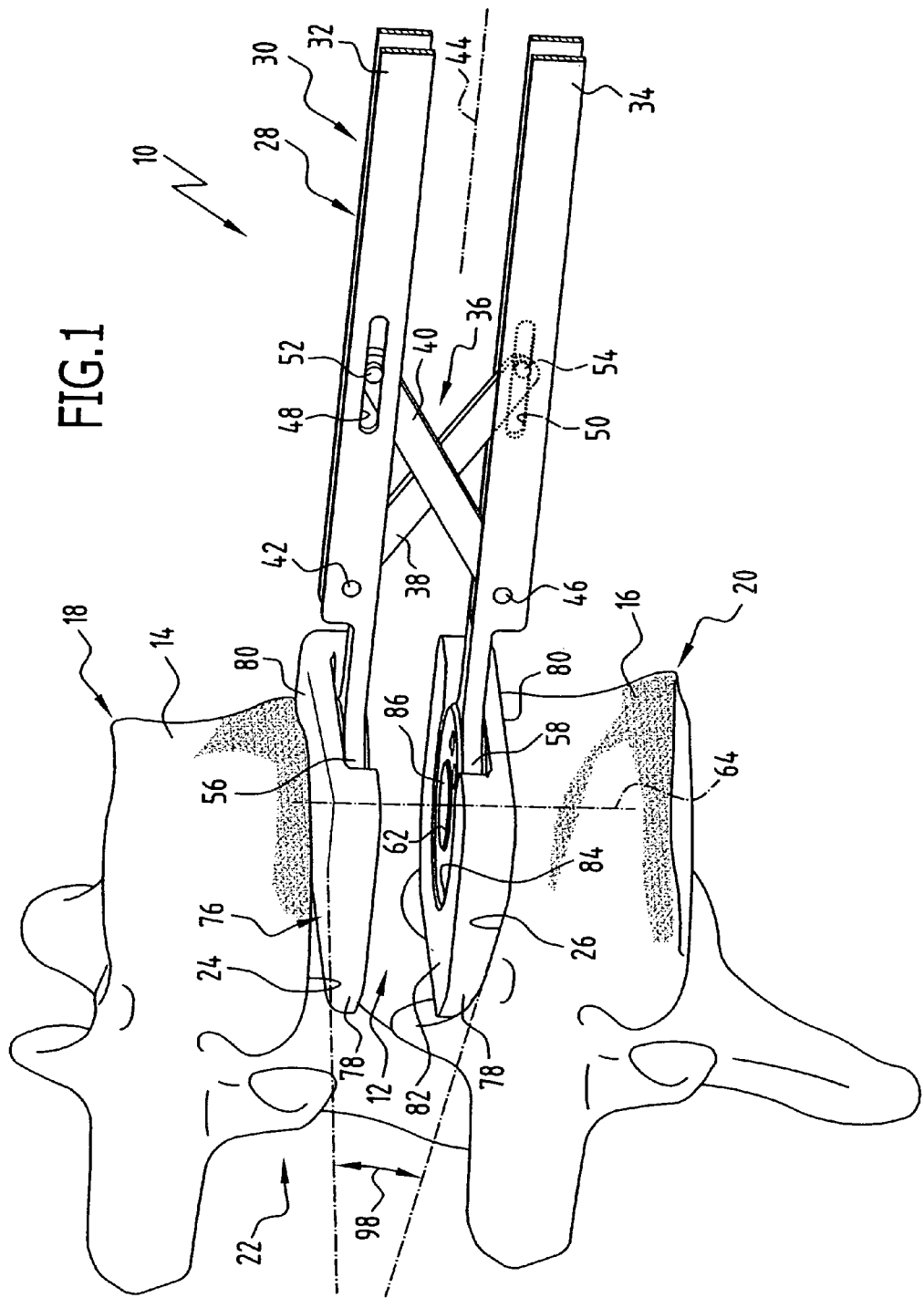
FIG. 1: a distal end of an instrument according to the invention with test implant plates inserted between adjacent vertebral bodies.

FIGS. 1 to 4 show a surgical instrument, which is provided as a whole with the reference character 10, for determining the size and/or height of an intervertebral implant which can be inserted into an intervertebral space 12 between two adjacent vertebral bodies 14 and 16 of two vertebrae 18 and 20 of a spinal column 22. The intervertebral implant is not shown in the drawings but typically comprises a first abutment element for abutment against a first articular surface 24 of the vertebral body 14 as well as a second abutment element, which is supported directly or indirectly, in particular movably on the first abutment element, for abutment against a second articular surface 26 of the vertebral body 16 facing the first articular surface 24.

The instrument 10 comprises an instrument part 28 in the form of a holding part, on the distal end of which a spreading device 30 is disposed. The spreading device 30 comprises two spreading jaws 32 and 34, which are aligned parallel to one another and connected to one another by a scissor element 36. The scissor element 36 comprises two links 38 and 40, wherein the link 38 is pivotably connected to the spreading jaw 32 by means of a bearing pin 42, the longitudinal axis of which is oriented transversely of a longitudinal axis 44 of the instrument part 28. In an identical manner, the link 40 is pivotably supported on a distal end of the spreading jaw 34 by means of a bearing pin 46, which is oriented parallel to the bearing pin 42. Each of the two spreading jaws 32 and 34 is provided with an elongate hole 48 and/or 50, which extends parallel to the longitudinal axis 44 and into which a guiding pin 52 and/or 54, which projects from the free end of the link 38 and/or 40 transversely of the longitudinal axis, engages and is guided. By means of the scissor element 36, a parallel movement of the two spreading jaws 32 and 34 is constrained. The spreading device 30 therefore forms a parallel retractor.

Disposed at the distal end on each of the spreading jaws 32 and 34 is a holding ring 56 and 58 respectively, which form abutment-element holding elements and each have a central bore 60 and/or 62 serving as a receiver. An axis of symmetry 64 of the holding rings 56 and 58 extends transversely of the longitudinal axis 44. The holding rings 56 and 58 are moreover each bored through twice, namely parallel to the axis of symmetry 64. Thus, in each case two adjusting bores 66 and 68 as well as 70 and 72 are formed in each holding ring 56 and 58. Longitudinal axes of the bore 60 and the adjusting bore 66 both cut the longitudinal axis 44, as do longitudinal axes of the bore 62 and the adjusting bore 70. The adjusting bores 68 and 72 are arranged offset in peripheral direction relative to the adjusting bores 66 and 70 by a setting angle 74, which in the present embodiment is 22°.

Also forming part of the instrument 10 is a test implant 76, which comprises two identical plates 78. The plate 78 is of a substantially cuboidal construction and has an abutment surface 80 for abutment against one of the articular surfaces 24 and/or 26. At an underside 82 substantially parallel to the abutment surface 80 and facing in the opposite direction, a cylindrical annular receiver 84 is incorporated, which is open laterally substantially in proximal direction. The diameter of the annular receiver 84 corresponds to an outside diameter of the holding rings 56 and 58. The annular receiver 84 is disposed coaxially with the axis of symmetry 64. Projecting likewise coaxially with the axis of symmetry 64 from the plate 78 is a holding pin 86, the outside diameter of which corresponds to the inside diameter of the bores 60 and 62. The holding pin 86 is provided in peripheral direction with an annular groove 88, fitted into which is an O-ring 90, the diameter of which is slightly larger than a depth of the annular groove 88 in radial direction. The annular groove 88 with the O-ring 90 fitted therein forms a clamping device, by means of which a connection of the plate 78 to one of the two holding rings 56 and 58 may be secured. Clamping occurs through elastic deformation of the O-ring 90 after the holding pin 86 has been introduced into one of the two bores 60 or 62. Projecting parallel to the holding pin 86 is a setting pin 92, the outside diameter of which corresponds to the inside diameters of the adjusting bores 66 to 72.

Figure 2:
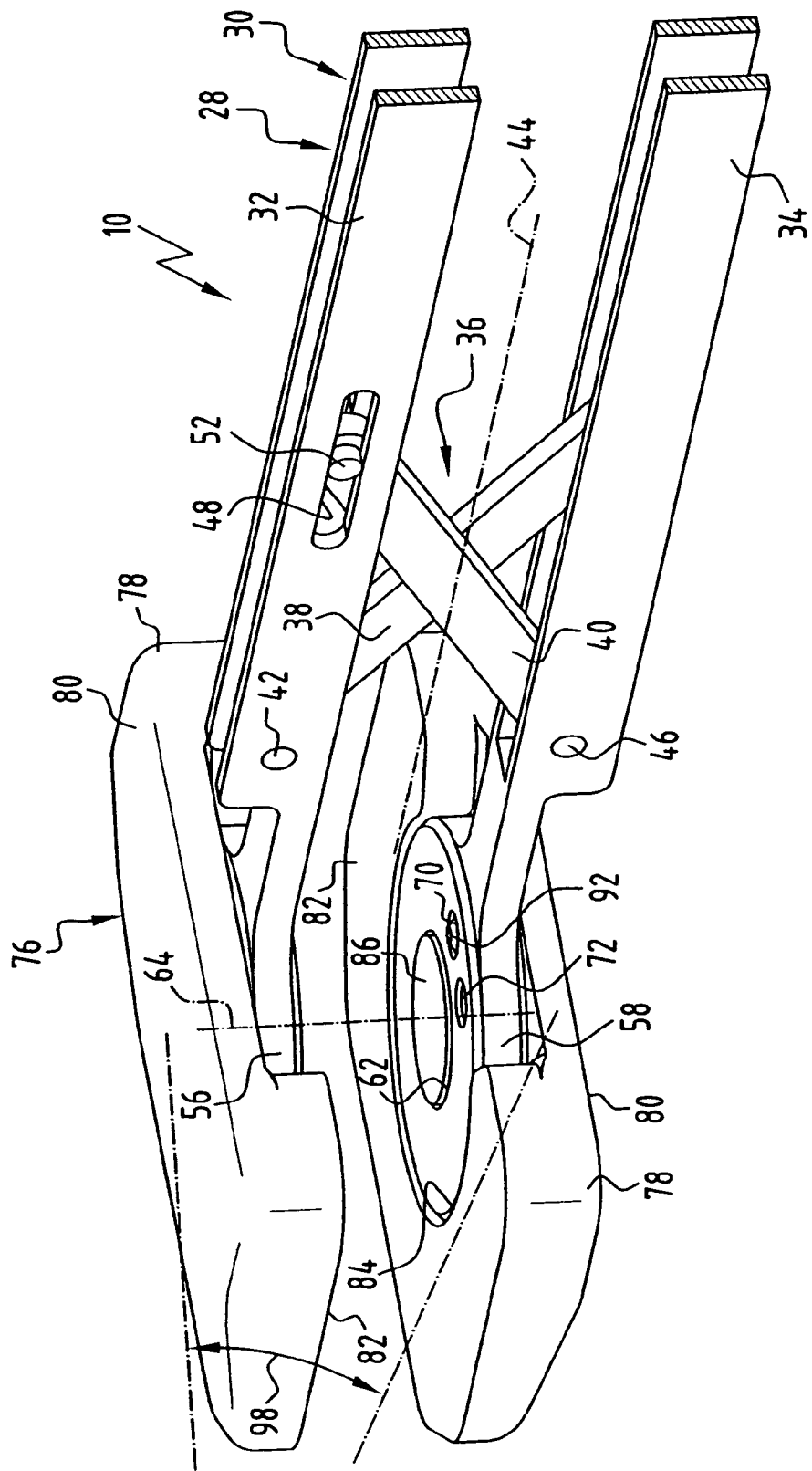
FIG. 2: an enlarged view of the distal end of the instrument with test implant plates held in a first angular position on the distal end of the instrument.
Figure 3:
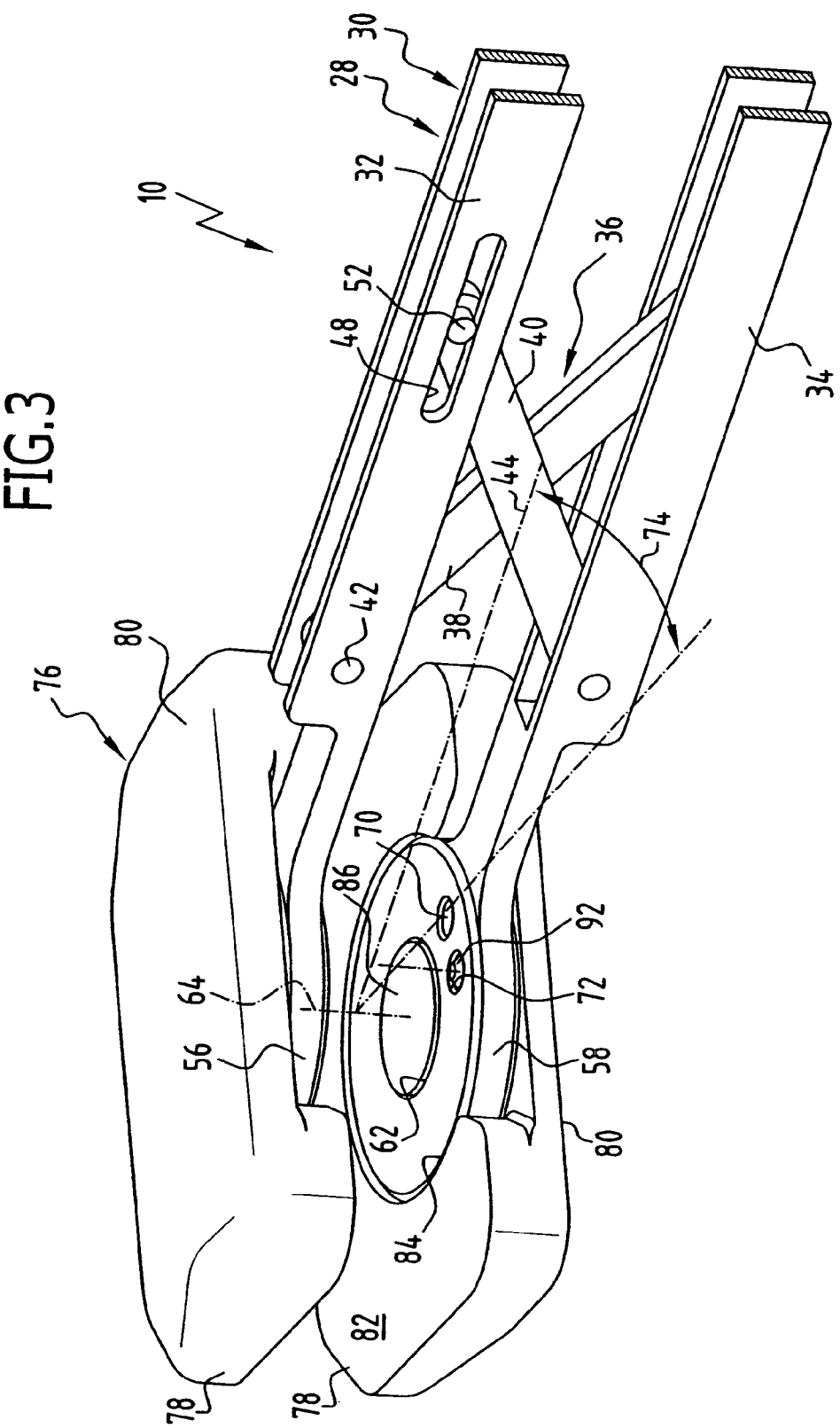
FIG. 3: a view similar to FIG. 2, only with the test implant plates held in a second angular position on the distal end of the instrument.

The plate 78 is designed in such a way that it may receive one of the holding rings 56 or 58, wherein the holding pin 86 is introducible into the bore 60 and/or 62 and the setting pin 92 is introducible into one of the adjusting bores 66 and 68 and/or 70 and 72. The plate 78 may therefore easily be moved parallel to the axis of symmetry 64, i.e. transversely of the longitudinal axis 44, into engagement with one of the holding rings 56 and 58. Once the two plates 78 have been connected to the holding rings 56 and 58 in such a way that the setting pins 92 engage into the adjusting bores 66 and 70, the result is an alignment of the plates 78 symmetrically relative to the instrument part 28 and/or to the longitudinal axis 44. Given such an angular setting of the plates 78 relative to the holding rings 56 and 58, which is shown in FIGS. 1 and 2, the instrument may then be used to introduce the test implant 76 through an anterior approach into a human or animal body and into the intervertebral space 12.

Introduction of the test implant 76 through a lateral approach is facilitated when the plates 78 are connected to the holding rings 56 and 58 in such a way that the setting pins 92 engage into the adjusting bores 68 and 72. The plates 78 are then connected to the holding rings 56 and 58 in a second angular position illustrated in FIG. 3 and assume a position rotated through 22° compared to the angular position illustrated in FIGS. 1 and 2.

In the embodiment illustrated in FIGS. 1 to 4, the wide holding rings 56 and 58 are aligned parallel to one another. It would also be conceivable for mutually remote annular surfaces 94 and 96 of the holding rings 56 and 58 to be inclined relative to one another. In this way, it is possible to set a specific lordosis angle 98, which the articular surfaces 24 and 26 define relative to one another.

The instrument 10 comprises not only the plates 78 illustrated in FIGS. 1 to 4 but also further, non-illustrated plates 78 of differing size and differing inclination of the abutment surfaces 80 relative to one another. By virtue of the differently inclined abutment surfaces 80, the lordosis angle 98 defined by the articular surfaces 24 and 26 may likewise be modeled. The plates 78 moreover also differ in height, so that intervertebral spaces 12 of differing height may be measured in a desired manner.

The instrument 10 is used during an operation as follows. First, a patient is positioned in a desired manner. In the case of a frontal approach, the patient may be positioned lying on his back. By means of the special positioning of the patient, a removal of the load on the spinal column may already be achieved.

In a next step, an approach is provided into the body of the patient, namely into the desired intervertebral space 12. The damaged intervertebral disk tissue is subsequently removed. Then the instrument 10 is suitably prepared. This means that in line with the anatomical conditions various test implants 76 of approximately matching size are prepared, namely with a corresponding height and natural lordosis angle 98. In accordance with the selected approach, anterior or lateral, the plates 78 of the test implant 76 are mounted onto the respective holding rings 56 and 58, i.e. with the setting pins 92 either into the adjusting bores 66 and 70 or 68 and 72. The instrument 10 is then introduced into the body of the patient, namely in such a way that the test implant 76 engages into the intervertebral space 12. Where necessary, by means of a drive device (not illustrated in detail) the spreading jaws 32 and 34 are moved apart from one another until the abutment surfaces 80 lie against the articular surfaces 24 and 26. If need be, the instrument 10 may be used to spread the adjacent vertebral bodies 14 and 16 further apart. Formed on the instrument part 28 is a non-illustrated display device comprising a scale, on which specific implant sizes are marked. Given an appropriate choice of plates 78, the implant to be selected may then be read directly off the scale. Alternatively, the scale may be a linear scale, so that from the displayed value a distance between the two articular surfaces 24 and 26 may be determined and the intervertebral implant to be inserted may be accordingly selected.

In a next step, the two spreading jaws 32 and 34 are moved back towards one another and the test implant 76 is removed from the intervertebral space 12.

What is claimed is:

1. A surgical instrument for determining at least one of the size and the height of an intervertebral implant insertable into an intervertebral space between two adjacent vertebral bodies of two vertebrae of a human or animal spinal column, the intervertebral implant having a first plate for abutment against an articular surface of one of the two adjacent vertebral bodies as well as a second plate supported directly or indirectly on the first plate for abutment against an articular surface of the other of the two adjacent vertebral bodies, the instrument comprising:

a holding part defining a longitudinal direction; and
   a test implant, which comprises a first test plate and a second test plate, each test plate having at least one abutment surface for abutment against one of the articular surfaces,
   wherein provided on a distal end of the holding part is a holding ring for detachable connection to the test implant, at least one of the first and the second test plates in relation to the longitudinal direction being detachably connectable to the holding ring in at least two defined, different angular positions relative thereto,
   wherein a first and a second connection element are provided for connecting the holding ring to one of the test plates, one of the test plates and the holding ring each carrying one of the connection elements, and
   wherein at least two setting elements are provided for defining and setting different angular positions of at least one of the first and the second test plates relative to the holding ring, the at least two setting elements configured for engagement with one another in the different angular positions, and at least one of the first and the second test plates having one of the setting elements and the holding ring having another of the setting elements.

2. The instrument according to claim 1, wherein the first or the second test plate in the different angular positions is disposed lying in each case in one plane and the two planes are identical.

3. The instrument according to claim 1, wherein at least one of the first and the second test plates and the holding ring, for detachable connection to one another, can be brought into engagement by means of a relative movement towards one another in a connection direction extending transversely of the longitudinal direction.

4. The instrument according to claim 1, wherein the holding ring is at least one of non-positively and positively connectable to at least one of the first and the second test plate.

5. The instrument according to claim 4, wherein a clamping device is provided for clamping and securing a connection of the holding ring to the first or the second test plate in one of the angular positions.

6. The instrument according to claim 1, wherein the first connection element is a receiver and the second connection element is a projection, which corresponds to the receiver and can be introduced therein.

7. The instrument according to claim 6, wherein the projection is a cylindrical pin, which projects from the test plate in the direction of the holding ring and the receiver is a bore or blind hole bore corresponding in diameter to the pin.

8. The instrument according to claim 1, wherein the projection can be introduced into the receiver in a direction transversely of the longitudinal direction.

9. The instrument according to claim 1, wherein a clamping device is provided for clamping and securing a connection of the holding ring to at least one of the first and the second test plates in one of the angular positions.

10. The instrument according to claim 9, wherein the clamping device comprises a clamping element, which at least partially embraces at least one of the first and second connection elements and which can be inserted into a gap between the holding ring and at least one of the first and the second test plates and before the connection of the holding ring and at least one of the first and the second test plates projects at one side beyond the gap.

11. The instrument according to claim 10, wherein the gap comprises an annular groove running in a peripheral direction around the projection, and the clamping element is an elastic ring, the diameter of which is larger than a depth of the annular groove.

12. The instrument according to claim 1, wherein a plurality of test implants are provided and that the plurality of test implants have different spacings between at least one of the abutment surfaces and different lordosis angles between the abutment surfaces.

13. The instrument according to claim 1, wherein at least one of the at least two setting elements is designed in the form of a setting receiver and at least one other of the at least two setting elements is designed in the form of a setting projection which can be introduced into the setting receiver.

14. The instrument according to claim 13, wherein the setting projection can be introduced into the setting receiver in a direction transversely of the longitudinal direction.

15. The instrument according to claim 13, wherein the test plate carries at least one setting projection and the holding ring has at least two setting receivers.

16. The instrument according to claim 1, wherein the holding ring is cylindrical in shape and a longitudinal axis of the holding ring extends transversely of the longitudinal direction.

17. The instrument according to claim 1, wherein the test plates each have a recess for the holding ring, and the holding ring can be introduced positively or substantially positively into the recess.

18. The instrument according to claim 1, wherein at least one of the first and the second test plates can be disposed in the second angular position relative to the holding ring by being rotated through a setting angle relative to the first angular position.

19. The instrument according to claim 18, wherein the setting angle has a value in a range of 10° to 30°.

20. The instrument according to claim 1, wherein a first and a second holding ring are provided on the distal end of the instrument and the first holding ring is detachably connectable to the first test plate and the second holding ring is detachably connectable to the second test plate.

21. The instrument according to claim 20, wherein the first holding ring and the second holding ring are supported such that they are movable towards or away from one another transversely or substantially transversely of their abutment surfaces.

22. The instrument according to claim 21, wherein the holding part has a path measuring device for measuring and indicating a spacing between the abutment surfaces or a displacement of the first and second holding rings relative to one another.

23. The instrument according to claim 20, wherein the distal end of the holding part has two spreading jaws, the spreading jaws comprising or carrying the first and second holding rings and the spreading jaws being movable away from or towards one another by means of a drive device, which is disposed on the holding part and comprises an actuating element disposed on the proximal end of the holding part.

24. The instrument according to claim 23, wherein the spreading jaws are supported such that they can be spread parallel to one another.

25. The instrument according to claim 1, wherein the holding ring comprises a closed circular body enclosing a circular bore.

* * * * *